United States Patent [19]
de Agudelo et al.

[11] Patent Number: 5,663,446
[45] Date of Patent: Sep. 2, 1997

[54] CATALYST FOR THE SIMULTANEOUS SELECTIVE HYDROGENATION OF DIOLEFINS AND NITRILES AND METHOD OF MAKING SAME

[75] Inventors: Magdalena Ramirez de Agudelo, Las Teques; Julia Guerra, San Antonio de Los Altos; Trino Romero, Caracas; Mariela Medina, Baruta, all of Venezuela

[73] Assignee: Intevep, S.A., Caracas, Venezuela

[21] Appl. No.: 585,950

[22] Filed: Jan. 16, 1996

Related U.S. Application Data

[62] Division of Ser. No. 354,969, Dec. 13, 1994, Pat. No. 5,523,271.

[51] Int. Cl.$^6$ .......................... C07C 209/00; C07C 17/20
[52] U.S. Cl. .............................................. 564/490; 570/260
[58] Field of Search ............................. 564/490; 570/260

[56] References Cited

FOREIGN PATENT DOCUMENTS

| 449144 | 2/1991 | European Pat. Off. . |
| 057196 | 9/1993 | Japan . |

*Primary Examiner*—Paul J. Killos
*Attorney, Agent, or Firm*—Bachman & LaPointe, P.C.

[57] ABSTRACT

A catalyst useful for the simultaneous and selective hydrogenation of diolefins and nitriles present in a hydrocarbon feedstock. The support material is preferably selected from the group consisting of an inorganic oxide-zeolite composite, carbon and zeolite. A catalytically active phase is deposited on the support material. The catalytically active metal phase is selected from the group consisting of partially reduced Group IB metals and completely reduced Group VIII metals. The catalytically active metal phase is present in an amount of $\geq 0.03$ wt %.

6 Claims, No Drawings

CATALYST FOR THE SIMULTANEOUS SELECTIVE HYDROGENATION OF DIOLEFINS AND NITRILES AND METHOD OF MAKING SAME

This is a division of application Ser. No. 08/354,969 filed Dec. 13, 1994, now U.S. Pat. No. 5,523,271.

BACKGROUND OF THE INVENTION

The present invention relates to a catalyst material for use in the hydrogenation of hydrocarbon feedstocks and, more particularly, a catalyst which is useful for the simultaneous and selective hydrogenation of diolefins and nitriles present in a hydrocarbon feedstock.

There are known in the prior art processes in catalysts for hydrogenating unsaturated compounds in liquid hydrocarbon feedstocks. For example, U.S. Pat. No. 4,152,351 discloses a process for the hydrogenation an olefinic unsaturation. More specifically, it relates to the catalytic hydrogenation of aliphatic, unsaturated compound in the presence of a palladium hydrogenation catalyst on a suitable support. Still more specifically, the invention relates to the use of applicable adjuvants for a palladium hydrogenation catalyst used to hydrogenate the olefinic unsaturation. Further, the invention relates to the hydrogenation of aliphatic, unsaturated compounds containing nitrile groups. U.S. Pat. No. 4,271,323 discloses a process for hydrogenating unsaturated compounds in the liquid phase in the presence of a soluble catalyst obtained by reacting an organo-metal derivative or a metal hydride with a synergistic mixture of (a) a compound of zinc, zirconium, manganese, molybdenum, or iron and (b) a nickel or cobalt compound. U.S. Pat. No. 4,734,540 discloses a process which is useful for the selective hydrogenation of polyunsaturated organic compounds. The resultant product of such a reaction produces the monoolefinic equivalents of the hydrogenated polyunsaturated organic compounds. The catalyst used in this selective hydrogenation process comprises nickel and sulfur deposited on the surface of an alumina support. The preferred catalyst does not contain halogens, noble metals, alkaline earth metals, or alkali metals and is characterized by having only a very low percentage of the total pore volume being provided by pores having an average pore diameter less than 150 angstroms. The great majority of the pore volume is present in the form of macropores having diameters of 500 to 1500 angstroms.

While the foregoing processes employ catalysts which are useful in the hydrogenation process, the processes and catalysts are not as selective nor do they simultaneously hydrogenate diolefins and nitriles. Naturally, it would be highly desirable to provide a catalyst which is useful for the simultaneous selective hydrogenation of diolefins and nitriles in a hydrocarbon feedstock.

Accordingly, it is the principle object of the present invention to provide a catalyst useful for the simultaneous and selective hydrogenation of diolefins and nitriles present in a hydrocarbon feedstock.

It is a further object of the present invention to provide a method for preparing a catalyst a aforesaid.

It is a still further object of the present invention to provide a process for the simultaneous and selective hydrogenation of diolefins and nitriles from a hydrocarbon feedstock employing such a catalyst.

Further objects and advantages of the present invention will appear hereinbelow.

SUMMARY OF THE INVENTION

The present invention relates to a catalyst useful for the simultaneous and selective hydrogenation of diolefins and nitriles present in a hydrocarbon feedstock. The support material is preferably selected from the group consisting of an inorganic oxide-zeolite composite, carbon and zeolite. A catalytically active phase is deposited on the support material. The catalytically active metal phase is selected from the group consisting of partially reduced Group IB metals and completely reduced Group VIII metals. The catalytically active metal phase is present in an amount of $\geq 0.03$ wt %.

The catalyst of the present invention is particularly useful in a process for the simultaneous and selective hydrogenation of diolefins and nitriles present in a hydrocarbon feedstock. The catalyst of the present invention is prepared by impregnating the support material with a solution of the active metal phase, drying the impregnated support and calcining. The dried and calcined support is thereafter activated to the proper reduction state. The catalyst is used in a hydrogenation process wherein the hydrocarbon feedstock in the presence of the catalyst and hydrogen is treated at a temperature of between about 50° to 250° C. and a pressure of 150 to 650 psi so as to selectively hydrogenate diolefins and nitriles from the hydrocarbon feedstock.

DETAILED DESCRIPTION

The catalyst of the present invention is particularly useful in a process for the simultaneous selective hydrogenation of diolefins and nitriles.

The catalyst of the present invention comprises a support material having a catalytically active metal phase deposited thereon. Suitable support materials include inorganic oxide-zeolite composites, carbon and zeolite. A particular useful support material for use in the catalyst of the present invention is a composite alumina-zeolite material disclosed in U.S. Pat. No. 4,762,537 and sold under the trademark Selexsorb by the Aluminum Company of America.

The support material has deposited thereon a catalytically active metal phase selected from the group consisting of Group IB metals and Group VIII metals of the Periodic Table. Depending on the active metal employed, the amount of the metal active phase present on the catalyst may vary. The active metal should be present in a minimum amount of about $\geq 0.03$ wt % up to 20 wt %. Particularly suitable active metal materials include copper, nickel and palladium.

As noted above, particularly suitable support material for use in the catalyst of the present invention is an alumina-zeolite composite sold by the Aluminum Company of America under the trademark Selexsorb. It has been found that the surface area of the resulting catalyst should be between about 100 to 1500 $m^2/g$, preferably between 100 to 1000 $m^2/g$ and ideally between about 250 to 350 $m^2/g$. The pore volume of the catalyst is preferably between 0.20 cc/g to 1.50 cc/g, preferably 0.30 cc/g to 0.70 cc/g.

In order for the catalyst of the present invention to be effective in the simultaneous selective hydrogenation of diolefins and nitriles, it has been found that the metal active phase must be reduced to the right state in order to be effective. In accordance with the present invention the Group IB metals must be partially reduced while the Group VIII metals must be completed reduced. By partial reduction it is meant that metal sites consist of one or more than one oxidation state different than zero, more particularly catalyst exhibit metal sites with a net charge on them. By complete reduction it is meant the metal sites largely consist on a single species, more particularly the highest number of species exhibit the elemental state of charge, i.e., 3000.

The catalyst of the present invention is prepared by impregnating the support material with a solution containing the catalytically active metal phase. As noted above the metal active phase should be present in an amount on the final catalyst of about $\geq 0.03$ wt %. The impregnated support material is thereafter dried and calcined at a temperature of between 150° and 600° C. for a time sufficient to decompose the metal salt impregnated on the catalyst support. Particularly suitable metal salts used in the aqueous solution for impregnating the catalyst material include $Cu(NO_3)_2 \cdot 2.5 H_2O$; $NiNO_3)_2$, $6H_2O$; $(CH_3COO)_2Pd$. The calcined catalyst is thereafter activated to the proper reduction state depending on the type of active metal phase employed. Partial reduction of the Group IB metals are accomplished under the following conditions: Temperature (°C.) 150–300, Pressure (psi) 15–150, $H_2$ flow rate (1t/h) 0.1–8.0. Complete reduction of the Group VIII is achieved under the following conditions: Temperature (°C.) 200–600, Pressure (psi) 15–150, $H_2$ flow rate (1t/h) 0.1–8.0.

The Catalyst of the present invention prepared in accordance with the method described above is particularly useful in processes for the simultaneous and selective hydrogenation of diolefins and nitriles from a hydrocarbon feedstock. The hydrocarbon feedstock in the presence of the catalyst is mixed with hydrogen wherein the ratio of the hydrogen to the diolefins and nitriles in the feedstock is less than three times stoichiometric amount required to selectively hydrogenate diolefins and nitriles. The hydrogen, hydrocarbon feedstock and catalyst are treated in a reactor at a temperature of between 50° to 250° C. at a pressure of between 150 to 650 psi. The preferred conditions for the hydrogenation process are a temperature of between 70° to 160° C. at a pressure of between 200 to 400 psi at a liquid hourly space velocity of between 0.1 to 5 $h^{-1}$, preferably 0.5 to 5 $h^{-1}$, ideally 1 to 4.5 $h^{-1}$.

The advantageous features of the catalyst of the present invention and method for preparing same will become clear from the following examples.

EXAMPLE 1

This example demonstrates the process for making the catalyst of the present invention employing an inorganic oxide-zeolite composite support having a Group VIII activated metal phase deposited thereon.

An alumina-zeolite composite support of the type disclosed in U.S. Pat. No. 4,762,537 and sold by Alcoa Aluminum Corporation under the trademark Selexsorb was selected as the catalyst support material. Four of the catalysts supports were impregnated with solutions of nickel nitrate of different concentrations. A fifth catalyst was prepared by impregnating the catalyst support with palladium. The five impregnated datalysts were dried and calcined so as to decompose the salts of the incorporated active metal. The calcined impregnated catalysts supports were then activated under controlled temperature and time conditions so as to completely reduce or partially reduce the active metal phase. For complete reduction, the catalysts were treated at a temperature of 450° C. at 250 psi for 8 hours. Partial reduction was carried out at 250° C. for 8 hours at 200 psi. Table 1 below sets forth the catalyst composition and activation treatment for each of the five catalysts.

TABLE 1

| Catalyst | Support | Active Metal Phase | Activation |
|---|---|---|---|
| 1 | alumina-zeolite | 0.93 wt % Ni | completely reduced |
| 2 | alumina-zeolite | 5.7 wt % Ni | completely reduced |
| 3 | alumina-zeolite | 5.7 wt % Ni | partially reduced |
| 4 | alumina-zeolite | 12.90 wt % Ni | completely reduced |
| 5 | alumina-zeolite | 0.30 wt % Pd | completely reduced |

EXAMPLE 2

This example demonstrates the catalyst activity for the catalysts of Example 1 for the simultaneous and selective hydrogenation of diolefins and nitriles present in hydrocarbon feedstocks.

The activity for the simultaneous selective hydrogenation was determined during a 4 hour run using a synthetic C5 hydrocarbon feedstock having the composition set forth below in Table 2.

TABLE 2

| Synthetic Feedstock Composition | |
|---|---|
| C5 | 97.5% |
| Propilonitrile | 0.5% |
| Diolefins | 0.5% |
| Monoolefins | 1.0% |

Eight cc's of each of the activated catalysts set forth in Example 1 were employed in a reactor for treating the hydrocarbon feedstock of Table 2. The reaction took place for 3 hours at a temperature of 120° C. and a pressure of 250 psi. The ratio by volume of hydrogen fed to the reactor with respect to the diolefins and nitriles was maintained at 3. The liquid space velocity (LHSV) of hydrogen feed was set at $3h^{-1}$. The results for each run employing the catalysts of Example 1 are set forth herein below in Table 3.

TABLE 3

| Catalyst | % Conversion Diolefins | % Conversion Monoolefins | % Conversion Nitriles |
|---|---|---|---|
| 1 | 100 | 59 | 86 |
| 2 | 100 | 78 | 100 |
| 3 | 0 | 0 | 0 |
| 4 | 100 | 0 | 100 |
| 5 | 100 | 0 | 88 |

As can be seen from Table 3 the concentration of the active metal phase of the Group VIII metal employed have an affect on the selective hydrogenation of the diolefins and nitriles in the hydrocarbon. Nickel concentrations of below 6 wt % were insufficient to insure selective hydrogenation. Catalyst 1 having a nickel concentration of 0.93 wt % was in fact not selective. At the same time, as can be seen from the results employing catalyst 5, 0.3 wt % palladium is sufficient for insuring selective hydrogenation of diolefins and nitriles. In addition, when comparing the results obtained from hydrogenation of feedstocks with catalysts 4 and 3, it can be seen that the Group VIII metals must be completely reduced in order for the catalyst to be active for the hydrogenation of diolefins and nitriles. Specifically, catalyst 3 which contained 5.7 wt % nickel partially reduced did not achieve any conversion of either olefins, monoolefins or nitriles.

EXAMPLE 3

This example demonstrates the process for making the catalyst of the present in invention employing an inorganic oxide-zeolite composite support having a Group IB active metal phase deposited thereon.

Four alumina-zeolite composite supports were impregnated with solutions of copper nitrate of different concentrations. The four impregnated catalysts were dried and calcined so as to decompose the salts of the incorporated active metal. Three of calcined impregnated catalyst supports were activated by carrying out partial reduction of the active metal phase at 250° C. for three hours. The fourth impregnated catalyst support was completed reduced under the same conditions set forth in

TABLE 4

| Catalyst | Support | Active Metal Phase | Activation |
| --- | --- | --- | --- |
| 6 | alumina-zeolite | 0.79 wt % Cu | partially reduced |
| 7 | alumina-zeolite | 5.9 wt % Cu | partially reduced |
| 8 | alumina-zeolite | 5.8 wt % Cu | completely reduced |

EXAMPLE 4

This example demonstrates the catalyst activity for the catalysts of Example 3 for the simultaneous and selective hydrogenation of diolefins and nitriles present in hydrocarbon feedstocks.

The synthetic feedstock set forth Table 2 of Example 2 was processed employing the catalysts of Example 3 under the same conditions described above in Example 2. The results of each run employing the catalysts of Example 3 are set forth hereinbelow in Table 5.

TABLE 5

| Catalyst | % Conversion Diolefins | % Conversion Monoolefins | % Conversion Nitriles |
| --- | --- | --- | --- |
| 6 | 98 | 0 | 21 |
| 7 | 99 | 0 | 82 |
| 8 | 0 | 0 | 0 |

As can be seen from Table 5, as was the case with the Group VIII metals discussed above, the concentrations of the active metal phase of the Group IB metals employed have an affect on the selective hydrogenation of the diolefins and nitriles in the hydrocarbon. Copper concentrations as low as 0.80 wt % were effective for the selective and simultaneous hydrogenation of diolefins and nitriles. In addition to the foregoing, the degree of reduction of the metal phase affects the activity of the Group IB metal. However, contrary to the Group VIII metals, the Group IB metals are effective when partially reduced and ineffective when completely reduced. In this regard see Catalyst No. 8 wherein the copper metal phase was completely reduced and no conversion of diolefins, monoolefins or nitriles was accomplished.

EXAMPLE 5

This example demonstrates the importance of the catalyst support on the activity of the catalyst of the present invention.

Carbon granules provided by Johnson Matthey were selected as one catalyst support. A second catalyst support comprising gamma alumina sold by Johnson Matthey under was likewise selected. Both of the supports were impregnated with palladium in the manner described above with regard to Example 1 and the impregnated catalyst supports were then activated by complete reduction at a temperature of 450° C., a pressure of 250 psi for eight hours. Table 6 below sets forth the catalyst composition and activation treatment for each of the two catalysts.

TABLE 6

| Catalyst | Support | Active Metal Phase | Activation |
| --- | --- | --- | --- |
| 9 | gamma alumina | 1.0 wt % Pd | completely reduced |
| 10 | carbon | 0.3 wt % Pd | completely reduced |
| 11 | gamma alumina | 0.3 wt % Pd | completely reduced |

EXAMPLE 6

In order to demonstrate the catalyst activity for the catalysts of Example 5 for the simultaneous and selective hydrogenation of diolefins and nitriles, the synthetic feedstock of Example 2 was treated with the catalysts under the same conditions set forth in Example 2. The results for each run employing the catalysts of Example 5 are set forth below in Table 7.

TABLE 7

| Catalyst | % Conversion Diolefins | % Conversion Monoolefins | % Conversion Nitriles |
| --- | --- | --- | --- |
| 9 | 100 | 88 | 18 |
| 10 | 100 | 0 | 50 |
| 11 | 100 | 30 | 20 |

The carbon supported catalyst, catalyst 10, was effective for the simultaneous hydrogenation of diolefins and nitriles in a selective manner wherein the gamma alumina supported catalysts (9 and 11) achieved no selective conversion of diolefins, monoolefins or nitriles. The results lead one to conclude that carbon and the zeolite present in the inorganic oxide-zeolite composite are effective catalyst supports for the catalysts of the present invention. Both the zeolite and carbon contain moderate Lewis acid sites which are believed to be responsible for the superior activity characteristics of the catalysts of the present invention.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

We claim:

1. A process for the simultaneous and selective hydrogenation of diolefins and nitriles from a hydrocarbon feedstock comprising:
   (a) providing a hydrocarbon feedstock having a diolefin content of ≧0.1 wt % and a nitrile content of ≧2 ppm(w);
   (b) providing a catalyst comprising 1) a support material selected from the group consisting of an inorganic oxide-zeolite composite, carbon and zeolite; and 2) a catalytically active metal phase selected from the group consisting of partially induced Group IB metals and completely reduced Group VIII metals, said active metal being present in an amount of about $\geq 0.03$ wt %;

(c) mixing the hydrocarbon feedstock in the presence of the catalyst with hydrogen wherein the ratio of hydrogen to the diolefins and nitriles in the feedstock is less than three times the stoichiometric amount required to selectively hydrogenate the diolefins and nitriles; and (d) treating the feedstock and hydrogen mixture in the presence of the catalyst at a temperature of about between 50° to 250° C. at a pressure of about between 150 to 650 psi.

2. A process according to claim 1 wherein said temperature is between about 60° to 160° C.

3. A process according to claim 2 wherein the pressure is between 200 to 400 psi.

4. A process according to claim 1 wherein the liquid hourly space velocity is in the range of between about 0.1 to 5 $h^{-1}$.

5. A process according to claim 1 wherein the liquid hourly space velocity is in the range of between about 0.5 to 5 $h^{-1}$.

6. A process according to claim 1 wherein the liquid hourly space velocity is in the range of between about 1 to 4.5 $h^{-1}$.

* * * * *